United States Patent
Wagner et al.

[11] Patent Number: 5,260,335
[45] Date of Patent: Nov. 9, 1993

[54] PHARMACEUTICAL PREPARATIONS FOR THE TREATMENT OF INFLAMMATORY DISEASES

[75] Inventors: Hildebert Wagner, Breitbrunn am Chiemsee; Walter Dorsch, Munich, both of Fed. Rep. of Germany

[73] Assignee: Plantamed Arzneimittel GmbH, Neumarkt, Fed. Rep. of Germany

[21] Appl. No.: 837,840

[22] Filed: Feb. 18, 1992

[30] Foreign Application Priority Data

Feb. 26, 1991 [DE] Fed. Rep. of Germany ....... 4106026

[51] Int. Cl.⁵ .......................................... A61K 31/235
[52] U.S. Cl. ..................... 514/532; 514/533
[58] Field of Search .................. 514/532, 533

[56] References Cited

PUBLICATIONS

Translation of relevant parts of Hoppe, Heinz, A., *Drogen kunde* Band 3 Supplement 8.Auflage, (1987), p. 235.
Translation of relevant parts of Hänsel, Rudolf, "Arzneimittel zur Selbstmedikation bei Heuschnupfen", *Deutsche Zeitung*, Nr. 35, (29 Aug. 1968), pp. 1293–1307.
Translation of relevant parts of *Homoopathisches Arzneibuch* 1. Ausgabe 1978, pp. 873–876.
Translation of relevant parts of Wagner, Hildebert, *Pharmazeutische Biologie Drogen und ihre Inhaltsstoffe*, (1988), pp. 240–270.
Translation of relevant parts of Negwer, Martin, *Organic-chemical drugs and their synonyms*, (1987), p. 122.
Translation of relevant parts of Neumüller, Otto-Albrecht, *Rompps Chemie-Lexikon*, (1987), pp. 3451–3452.
Translation of relevant parts of Neumüller, Otto-Albrecht, *Rompps Chemie-Lexikon*, (1990), p. 1475.
Kilkuskie, R. E. et al. "Characterization of Tannins Containing Anti-HIV Activity" in Annals of the New York Academy of Sciences, vol. 616, New York, (1990), pp. 542–544.
Nishizawa et al., "Anti-AIDS Agents, I. Isolation and Characterization of Four New Tetragalloylquinic Acids as a New Class of HIV Reverse Transcriptase Inhibitors From Tannic Acid", *Journal of Natural Products*, vol. 52, No. 4, Jul–Aug 1989, pp. 762–768.

Primary Examiner—Marianne M. Cintins
Assistant Examiner—John Peabody
Attorney, Agent, or Firm—Cohen, Pontani, Lieberman, Pavane

[57] ABSTRACT

The invention concerns pharmaceutical preparations containing at least one of the following compounds as an active ingredient either alone or in any desired combination: gallic acid, methyl gallate and compounds of the general formula

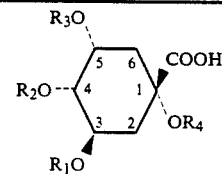

| | $R_1$ | $R_2$ | $R_3$ | $R_4$ |
|---|---|---|---|---|
| 1 | galloyl | galloyl | galloyl | H |
| 2 | galloyl | digalloyl | galloyl | H |
| 3 | galloyl | galloyl | digalloyl | H |
| 4 | digalloyl | galloyl | galloyl | H |
| 5 | galloyl | galloyl | galloyl | galloyl | with galloyl signifying the radical

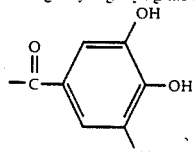

and digalloyl signifying the radical

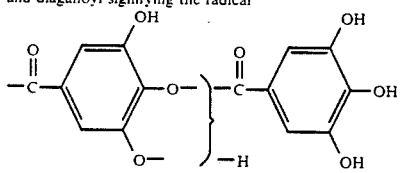

and the pharmaceutically acceptable salts, ethers and esters thereof. The invention further relates to a method for isolating the aforementioned compounds from the plant Galphimia Glauca. The drugs according to the invention are effective antiphlogistic agents.

13 Claims, No Drawings

PHARMACEUTICAL PREPARATIONS FOR THE TREATMENT OF INFLAMMATORY DISEASES

The invention concerns pharmaceutical preparations containing at least one compound selected from gallic acid, methyl gallate and certain tetragalloylquinic acids as well as methods for isolating them from plant material.

The pharmaceutical preparations are useful for the treatment of inflammatory diseases of all organs, in particular for rheumatic diseases, allergic and immunological diseases, bronchial asthma and other pulmonary diseases such as obstructive bronchitis and inflammatory skin diseases (antiphlogistic agents).

The term inflammation, as it is to be understood here is generally understood as a reaction of the organism and its tissues to various harmful stimuli. Harmful stimuli are exogenic and endogenic stimuli, such as for instance tissue injuries, penetration by foreign bodies, chemical substances, bacterial toxins, allergens, immune complexes, microorganisms, pathological metabolic products and decomposition products of tumors. The classical symptoms, pain and fever, are closely related to the inflammation process.

It has been known for a long time that certain substances produced by the body, the so-called mediators, are closely related to the inflammation process. These mediators, which are of extremely great pathogenetic importance, are released from the body's cells by the harmful event (noxe). The most important and best-known mediators are considered to be histamine, 5-HT (5-hydroxytryptamine), bradykinin, the prostaglandins, the prostacyclins, the leukotrienes, thromboxanes and the only recently characterized platelet activating factor (PAF).

These and other mediators, which are not specified individually in detail, have an extremely great effect on the contraction of the smooth muscle, they lead to disorders of cardiac function and impair the integrity of the blood vessels and mucous membranes, such as, for example, those of the bronchial system. They also cause the aggregation of platelets and polymorphonuclear leukocytes with the severe effects of anaphylactic constriction of the airways, blood pressure reduction, cardiac arrhythmias, plasm exudation, tissue edema, hemoconcentration, thrombocytopenia, leukocytopenia, clumping of platelets and polymorphonuclear leukocytes in the pulmonary capillaries as well as highly severe respiratory disorders and circulatory collapse.

Owing to their broad pharmacological spectrum of action their wide distribution in the organism, their formation by numerous physical, chemical, pathological, pathophysiological and pharmacological influences, as well as owing to their involvement in a large number of pathophysiological processes, the mediators and the influencing thereof by means of pharmaceuticals are of utmost medical significance (cf. "The Pharmacological Basis of Therapeutics, ed. Goodman and Gilman, 6th edition, 1980, Macmillan Publishing Company).

PAF appears to enjoy special importance in the pathogenesis of inflammatory and allergic processes.

PAF is a glycerophosphocholine with the chemical name 1-0-alkyl-2-acetyl-sn-glyceryl-3-phosphorylcholine. This factor is released by a number of cells, such as macrophages, basophilic and neutrophilic granulocytes, and others, when activated. The release of PAF leads thereafter to the pathological conditions described above and probably to a number of other, hitherto not fully understood, pathological symptoms. PAF need not have a direct effect, rather it may develop its effect by stimulating other mediators. Recent studies have shown that PAF plays an important role in particular in causing clinical bronchial asthma and in other pathological conditions of the lungs, e.g. obstructive bronchitis.

In addition to its important role in causing bronchial asthma and in anaphylaxis, PAF is to be considered a highly potent inflammation mediator possessing the pathological effects already described above.

A large number of the mediators named above, including PAF, are released by a membrane-linked phospholipase from phospholipids of the cell membrane, forming arachidonic acid, on the one hand, and a preliminary stage of PAF, on the other.

Two groups of mediators are formed originating from arachidonic acid:
(i) by the enzyme, cyclooxygenase, the prostaglandins including prostacyclin and thromboxane,
(ii) by the enzyme, lipoxygenase, the open chain hydroperoxy and hydroxy acids and, in particular, the leukotrienes.

The preliminary stage of PAF is transferred into the active compound by an acetyltransferase.

Two groups of active substances are pharmacologically important in the treatment of inflammation; these are, on the one hand, the so-called nonsteroidal antiphlogistic agents, that is compounds and derivatives of salicylic acid. Other compounds with a well-known antiphlogistic action are the pyrazolone derivatives, the para-aminophenol derivatives, the indole derivatives (e.g. indomethacin) and the derivatives of propionic acid.

The pharmacological action of all these compounds is based on the fact that they can inhibit cyclooxygenase and thus prevent the synthesis of prostaglandins or thromboxanes.

Salicylic acid and its derivatives and the further compounds of the whole class are burdened by a number of severe and highly severe side effects. Prolonged administration of salicylic acid derivatives, for instance, leads to gastric and intestinal ulcers. The relative intolerance of the pyrazolone derivatives, the hepatotoxic effect of the para-aminophenol derivatives, the general intolerance of indomethacin and the ulcerative effect of the propionic acid derivatives are also well-known.

A further severe disadvantage of nonsteroidal antiphlogistic agents is that they enhance, under certain circumstances, the pathological effect of the mediators, as the inhibition of the cyclooxygenase provides more substrate for lipoxygenase and thus for the formation of leukotrienes (substrate shift).

The nonsteroidal antiphlogistic agents are contrasted by the steroidal antiphlogistic agents, that is the corticosteroids and their derivatives. The antiphlogistic action of the corticosteroids is based on their ability to inhibit both phospholipase and lipoxygenase, thus inhibiting the entire arachidonic acid metabolism. The unfortunate side effects are a disadvantage for therapy with corticosteroids, and only the following are to be mentioned as examples: duodenal or ventricular ulcers, myopathy, osteoporosis, mental disorders, increased susceptibility to infection, subcapsular cataracts and similar.

In addition to the corticosteroids, selective lipoxygenase inhibitors such as benoxaprofen are in use. This class of substances is also burdened with severe side affects, such as fatal exfoliative dermatitis (scalded skin syndrome). Compounds of the following general formula are described in Journal of Natural Products Vol. 52, No. 4, pp 762-768 (1989).

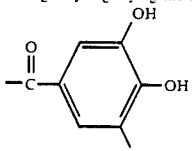

|   | $R_1$ | $R_2$ | $R_3$ | $R_4$ |
|---|-------|-------|-------|-------|
| 1 | galloyl | galloyl | galloyl | H |
| 2 | galloyl | digalloyl | galloyl | H |
| 3 | galloyl | galloyl | digalloyl | H |
| 4 | digalloyl | galloyl | galloyl | H |
| 5 | galloyl | galloyl | galloyl | galloyl | with galloyl signifying the radical

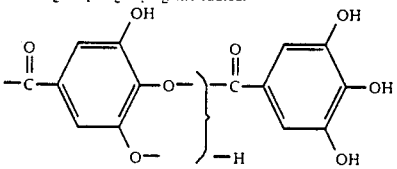

and diagalloyl signifying the radical

It is said that these compounds inhibit the HIV Reverse Transcriptase and DNA polymerase in vitro. The compounds methyl gallate and gallic acid are also known per se (cf. The Merck Index, 9th Edition 1976).

The general formula includes several stereoisomeric compounds which differ as to the position of the groups $R_4O$, $R_2O$ and $R_3O$.

The inventors have now surprisingly discovered that a pharmaceutical preparation containing at least one compound selected from the group consisting of tetragalloylquinic acids according to the above indicated general formula, methyl gallate and gallic acid and the pharmaceutical salts, ethers and esters thereof, possess an excellent antiphlogistic action. These compounds can be isolated from the plant Galphimia glauca.

By the subject of the present invention, and included by the general formula, are all isomeric compounds.

The compound, tetragalloylquinic acid, in which the radicals $R_1$ to $R_4$ signify galloyl, enjoys particular preference.

The subject of the invention therefore are pharmaceutical preparations containing at least one of the following compounds or any combination thereof:
gallic acid
methyl gallate
compounds of the general formula
and the pharmaceutically acceptable salts, esters and ethers thereof.

The most effective as regards the asthma-protective action is tetragalloylquinic acid or a salt ester or ether thereof. A combination of all the compounds named above is also highly effective.

A further subject of the invention are methods for isolating the aforementioned compounds from Galphimia glauca.

The term "pharmaceutical preparations" also includes plant extracts on an aqueous or nonaqueous basis or on the basis of a pharmaceutically acceptable solvent, if necessary together with other carriers, dilution media and additives which are well-known in the field of pharmaceutical technology and which may contain at least one of the aforementioned compounds alone or in any combination.

Essentially, such an extract contains, for instance in an aqueous base, the active substances gallic acid, gallic acid methyl ester and tetragalloylquinic acid in a quantitative ratio of about 2.5:2.5:10.

The pharmaceutical preparations according to the invention possess the essential and important property of blocking inflammatory processes of allergic pathogenesis, particularly PAF-induced effects such as, for example, obstructive bronchitis, bronchial asthma, inflammatory pulmonary diseases, angiological disorders, inflammatory vascular processes, inflammatory skin diseases, etc.

Most preferably the pharmaceutical preparations according to the invention are suitable for the prophylaxis and therapy of allergic and PAF-induced bronchial asthma.

Therefore, the pharmaceutical preparations according to the invention have the property of steroidal antiphlogistic agents but do not display their unfortunate side effects and are therefore generally valuable for the prophylaxis and treatment of inflammatory processes in the broadest sense in the development of which the well-known mediators, such as prostaglandins, histamine, PAF, leukotrienes and thromboxanes play a role.

In contrast to the non-steroidal antiphlogistic agents, which do not act against the leukocyte-induced effects of chronically inflammatory diseases, as they do not inhibit leukotriene formation, the compounds used here are also superior to the well-known compounds in this respect owing to their surprising, excellent and beneficial action.

The pharmaceutical preparations according to the invention fulfil the requirement for non-steroidal antiphlogistic agents which inhibit the synthesis of the leukotrienes and prostaglandins and thromboxanes and counteract the effects of the PAF factor. They are free from the disadvantages connected with the steroidal or non-steroidal antiphlogistic agents.

The pharmaceutical preparations according to the invention have not been shown to have any toxicity to date.

The compounds indicated above or a pharmaceutical preparation thereof can be administered in small doses to obtain a therapeutic, antiinflammatory effect.

The pharmaceutical preparations according to the invention can be used for the treatment of inflammations of the joints, the skin, the mucous membranes and inner organs, irrespective of whether the inflammation was caused by infective agents, immunological processes or traumata. In this context, inflammatory processes of the bronchial system in particular, such as bronchial asthma or obstructive bronchitis, are particularly advantageously treated indications. In addition, the drugs according to the invention can be used for the prophylaxis and treatment of vascular and cardiac diseases in which it appears desirable to inhibit the biosynthesis of inflammatory substances by platelets. The drugs according to the invention can be used to particular advantage for the prophylaxis and treatment of all PAF- and/or leukotriene-induced phenomena and, in particular, for the treatment of the bronchial region.

The necessary quantity of the compound to be used (hereinafter referred to as the active ingredient) in the drug for the desired therapeutic effect depends on the respective compound, the mode of administration, the subject to be treated with it, and the respective illness. A suitable dose of a compound for administration to a mammal suffering from an inflammation, a painful or feverish condition, as described above, is about 0.1 μg to 500 mg of the active ingredient per kilogramme of body weight. In the case of systemic administration the dose may be in the range of 0.5 to 500 mg of the active compound per kilogramme of body weight and the most preferred dose in the range of 0. 5 to 50 mg per kilogramme of body weight, e.g. 5 to 25 mg per kilogramme of body weight given, if necessary, several times a day, particularly two or three times a day.

In the case of topical administration, e.g. on the skin or mucous membranes, the suitable dose may be considerably larger.

Although it is, in principle, possible to administer the active ingredient(s) alone, it is to be preferred to administer the active ingredient in the form of a pharmaceutical formulation containing a compound, as described above, and a pharmaceutically acceptable carrier substance for it. Generally, the active ingredient is present in such a formulation in a concentration of 0.1 to 99.9 weight % of the formulation. A single dose of the formulation generally contains between 0.1 mg and 1 g of the active ingredient. For topical administration, the concentration of the active ingredient is preferably 1 to 2 weight % of the preparation, but the active ingredient may account for up to 10 weight %. Preparations intended for nasal or buccal administration, such as, for example, self-atomizing powders, sprays or other well-known and conventional devices, may contain 0.1 to 20 weight %, e.g. 2 weight % of the active ingredient.

The pharmaceutical preparations according to the invention for use in both veterinary and human medicine contain the active ingredient together with a pharmaceutically acceptable carrier substance and, if necessary, other therapeutically active ingredients. The carrier substance must be acceptable in the sense that it is compatible with the other ingredients of the formulation and has no disadvantageous effect on the recipient of the formulation.

Suitably, the formulations are available in the form of an oral, ophthalmological, rectal, parenteral (including subcutaneous, intramuscular and intravenous), intraarticular, tonical, nasal or buccal dosage form.

The formulations according to the invention are generally available in the form of a single dose and can be manufactured by any well-known method in the field of pharmaceutical technology. Essentially, all the methods contain the step of joining the active ingredient with the carrier substance, if necessary with one or more additional ingredients. As a rule, the formulations are manufactured by even and intensive mixing of the active ingredient with a liquid carrier or a finely distributed solid carrier or both, and then, if necessary, shaping of the product in the desired preparation form.

The formulations according to the invention for oral administration may be available in the form of discrete units, such as, for example, capsules, cachets, tablets or pastilles, with each form containing a certain quantity of the active ingredient. They may also be available in the form of a powder or in the form of a granulate or in the form of a solution or a suspension in an aqueous or nonaqueous liquid, or in the form of an oil-in-water emulsion or a water-in-oil emulsion. The active ingredient may also be available in the form of a bolus, an electuary or a pasta.

If the preparations according to the invention are available in the form of a tablet, this can also be manufactured by compressing or casting the active ingredient, if necessary together with one or more additional ingredients. Compressed tablets can also be manufactured by compressing the active ingredient in a free-flowing form, e.g. as a powder or granulate, if necessary mixed with a binding agent, a lubricant, an inert dilution agent, surface active or dispersion medium in a suitable device. Cast tablets can be manufactured by casting a mixture of the active ingredient in powder form and a suitable carrier substance moistened with an inert liquid dilution agent in a suitable device.

The preparations according to the invention for rectal administration may be available in the form of suppositories with the active ingredient contained in a carrier, e.g. made of cacao butter. It may also be available in the form of an enema.

If the formulations according to the invention are intended for parenteral administration they generally contain a sterile aqueous preparation of the active ingredient which is preferably isotonic with the blood of the recipient.

Preparations according to the invention which are suitable for intraarticular administration may be available in the form of a sterile aqueous preparation of the active ingredient with the active ingredient, if necessary, in microcrystalline form, e.g. in the form of an aqueous microcrystalline suspension.

The formulations according to the invention may also be available in the form of a liposomal preparation or in the form of a biodegradable polymer system for administration of the active ingredient.

Formulations according to the invention suitable for topical administration contain liquid or semi-liquid preparations, such as, for example, liniments, lotions, dressings, oil-in-water or water-in-oil emulsions, such as, for example, creams, ointments or pastes, or solutions or suspensions, such as, for example, drops. For instance, the active ingredient for ophthalmological administration may be available in the form of aqueous eye drops, for example in the form of a 0.1 to 1.0 % solution.

Formulations according to the invention for administration through the nose or into the buccal cavity are available in the form of a self-atomizing powder or in the form of spray preparations, e.g. as an aerosol. The formulations preferably yield a particle size in the range of 1 to 200 μm after dispersion.

Formulations according to the invention may contain the active ingredient also in an aqueous or diluted alcoholic solution. The active ingredient can, if necessary, be converted into a fine mist by a spray device and inhaled by the patient.

Pharmaceutical preparations of this type generally contain a flavouring, such as, for example, sodium saccharin and a volatile oil. Also a buffer substance and/or a surface active agent may be contained in such preparations together with preservatives, such as, for example, methyl hydroxybenzoate.

Other preparations suitable for administration through the nose consist of a coarse powder displaying a particle size of 20 to 500 μm which is administered in the same way as snuff.

In addition to the ingredients mentioned above, the formulations according to the invention may contain one or more additional conventional and well-known components, such as, for example, dilution agents, buffer substances, flavourings, binding agents, surface active agents, thickening agents, lubricants, preservatives, antioxidants, emulsifiers and similar.

The following examples explain the invention without limiting it to the examples.

EXAMPLE 1

Isolation of an extract from Galphimia glauca

Galphimia glauca (Thyrallis glauca) is a plant of the Malpighiaceae family and is native to Central America.

In order to isolate the compounds described above, one starts with the dried plant, first extracting it exhaustively with alkanols with 1 to 3 carbon atoms, such as methanol, ethanol and/or propanol, particularly with methanol, using the well-known methods. This can take place using Soxhlet extraction, percolation or maceration. In addition, supercritical gases (e.g. $CO_2$ or butane) can be used according to well-known methods for extraction (fraction I). After removing at least one part, preferably of the whole extraction medium, the more lipophilic portions are separated from the extract by taking up the extract with water and extracting the mixture with chlorinated hydrocarbons with a boiling point of not more than 120° C., particularly with chloroform and/or methylene chloride (fraction III). The remaining aqueous phase is extracted with esters of the acetic acid with alkanols with 1 to 4 carbon atoms, e.g. methyl, ethyl, propyl and/or butyl acetate, particularly with ethyl acetate; here an intermediary polar fraction passes over into the acetic ester phase and is isolated (fraction II). From this fraction, the more hydrophilic ingredients are separated and this in particular by means of flash chromatography using silica gel as a stationary phase with methylene chloride/acetone/methanol/formic acid as elution media; a typical elution medium contains 90% methylene chloride, 10% acetone and 10% -methanol to which 1% of formic acid is added. The fraction which passes over first is, if necessary, processed further (extract); the subsequently appearing, more hydrophilic fraction contains only flavone glycosides and is pharmacologically ineffective.

The more lipophilic fraction obtained in the chromatography described above contains, according to the thin-layer chromatogram, mainly gallic acid, gallic acid methyl ester, quercetin and several by-products. In order to separate the formic acid it contains, approx. 20 ml of distilled water is added to the fraction, which is relieved gently of the organic solvent using the rotary evaporator. The aqueous formic acid solution was then transferred to a column packed with RP material and equilibrated with water. The formic acid was eluted through water and the active substances sought adhered to the beginning of the column. They were eluted from the column with 70% methanol, and the remaining methanol was evaporated off. The remaining aqueous solutions were lyophilized.

In the thin-layer chromatography or HPLC chromatography described above the following materials and methods were used.

(a) Thin-layer chromatography:
Adsorbents:
  silica gel 60 F 254 finished plates 20×20 cm;
  layer thickness: 0.25 cm;
Migration system DC-G 1:
  toluene-acetone-formic acid (55:30:4.5);
Detection medium:
  det-1 (phenols): $FeCl_3$ (5% in 0,1 n HCl);
  det-2 (flavonoids and vegetable acids): natural substance reagent acc. NEU (1% in methanol) subsequently sprayed with PEG 400 solution (5% in ethanol);

(b) HPLC:
Adsorbents:
  column: Hibar 125-4 Lichrospher 100 CH-18/2 (5 μm);
Separation systems:
  HPLC-G 1: gradient: 4–20% in 30 min., linear rise;
  HPLC-G 2: gradient: 4–30% in 30 min., 30–70% in 10 min., linear rise;
Solvents:
  A: water;
  B: acetonitrile;
  in each case adding 10 ml of 0,1 n phosphoric acid/l;
Detection:
  in each case at 265 nm.

Isolation of the tetragalloylquinic acid

In order to isolate the tetragalloylquinic acid, fraction II is first hydrolyzed by adding HCl (16% HCl; 15 min, 60° C.). The mixture is then isolated through a silica gel column using a solvent system consisting of ethyl acetate/methanol/water/formic acid (85:10:3:0.5) and by preparative HPLC through RP material using acetonitrile/water as the solvent system. The isolated compound was identified and characterized as tetragalloylquinic acid by means of $^1$H-NMR and $^{13}$C-NMR analyses.

EXAMPLE 2

Biological tests

Male white guinea pigs were sensitized by means of intraperitoneal and intramuscular injection of ovalbumin according to the well-known methods [1]. Inhalation stimulus experiments were conducted 4 to 6 weeks later.

All the experiments were conducted according to a randomized evaluation record [2]:

Groups of 10 to 14 animals were divided into two sub-groups and either treated with the material to be studied or with control solutions. After one week, the animals were treated a second time, with those which had been given the control being given the active compound and vice-versa (each animal was once given either the plant extract, the fraction or compound to be tested or the corresponding solvent).

1 hour, 12 hours, 4 or 7 days after the pretreatment, the animals were exposed to various inhalation stimuli. Ovalbumin, histamine hydrochloride and acetylcholine were dissolved in physiological saline solution (1:99, 1:999, 1:99 w/v) PAF first in ethanol and then in saline solution containing 0.25% BSA dissolved to a final concentration of 1 μg PAF/ml. Ovalbumin, PAF, histamine and acetylcholine were administered as an aerosol atomized by ultrasound.

Spontaneously breathing animals were placed in a dual-chamber body plethysmograph in which the two chambers were separated around the head of the animals by a rubber collar filled with water. Changes in volume in the two chambers were measured by means of pressure transfer systems. The degree of bronchial obstruction was determined by means of the parameter, "compressed air". This technique is ten times more sensitive than other invasive methods (Dorsch et al., Pflugers Arch., 1981, 391: 236 to 241).

The action of the plant extracts or of the compounds on the PAF-induced reaction was studied by means of the successive inhalation of histamine, PAF and histamine:

One group of animals was divided into two sub-groups and both sub-groups inhaled histamine in a concentration causing a moderate bronchial obstruction. One hour later, one group was given the substances to be studied, the other group was given the solvent alone. Both groups were subjected 12 hours later to a stimulus by means of the successive inhalation of PAF and histamine with 1 μg PAF at first and, 60 minutes later, the same dose of histamine being given as before. The second histamine stimulus usually leads to asthmatic reactions in control animals which are three times as severe as the first time (Dorsch et al., Int. Arch. Allergy Appl. Immunol., 88: 228 to 230 (1988)).

The results of these experiments are shown in table 1. The results shown in the table show that fraction I and fraction III possess no significant activity. By contrast, fraction II is able to inhibit both allergic and PAF-induced bronchial asthma by more than 50% when a concentration of 30 mg/kg is administered. Fraction II contains gallic acid, gallic acid methyl ester, tetragalloylquinic acid and quercetin. Subfraction II/1 shows the same results and is also able to inhibit both allergic and PAF-induced bronchial asthma by more than 50% when a concentration of 30 mg/kg is administered. The individual compounds, methyl gallate, gallic acid and quercetin, display about the same activity in preventing bronchial obstruction after inhalation of an allergen and, in the case of PAF-induced bronchial obstruction, methyl gallate displays somewhat more activity than the mixture of quercetin, gallic acid and protocatechinic acid. The greatest activity was shown by the tetragalloylquinic acid compound which inhibits with a low oral dose of 5 mg/kg the bronchial reactions to an allergen stimulus by 86±24% and a PAF-induced bronchial reaction by about 60%.

Literature:

[1] Dorsch et al., Plugers Arch. 391: 236–241 (1981)
[2] Dorsch et al., Naunyn-Schmiedebergs Arch. Pharmacol. 325: 275–282 (1984)

TABLE 1

| Fraction/Compound | Concentration (mg/kg) | % inhibition of bronchial obstruction after allergen inhalation 1st stimulus (%) | 2nd stimulus (%) | PAF inhalation (%) |
|---|---|---|---|---|
| Fraction II | 30 | 55 ± 52 | 54 ± 28 | 51 ± 32 |
| Fraction I | 30 |  |  | 12 ± 35 |
| Fraction III | 30 | 19 ± 68 | 22 ± 65 | 18 ± 24 |
| Subfraction II/1 | 30 | 59 ± 32 | 43 ± 46 | 57 ± 29 |
| Methyl gallate | 45 | 43 ± 34 | 41 ± 24 | 65 ± 24 |
| Gallic acid | 45 | 37 ± 35 | 40 ± 31 |  |
| Tatragalloyl-quinic acid | 5 | 86 ± 24 | 57 ± 79 | 60 ± 43 |
| Quercetin | 45 | 53 ± 23 | 34 ± 33 |  |
| Mixture | 45 |  |  | 36 ± 45 |
| Fraction II (3 days 3 × 2 mg/kg) |  | 75 ± 63 |  | 71 ± 38 |

We claim:

1. A method of treating inflammatory diseases, by administering an antiphlogistic pharmaceutical preparation comprising at least one compound selected from the group consisting of compounds of the general formula:

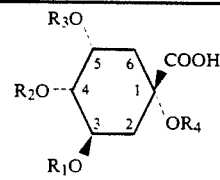

| | $R_1$ | $R_2$ | $R_3$ | $R_4$ |
|---|---|---|---|---|
| 1 | galloyl | galloyl | galloyl | H |
| 2 | galloyl | digalloyl | galloyl | H |
| 3 | galloyl | galloyl | digalloyl | H |
| 4 | digalloyl | galloyl | galloyl | H |
| 5 | galloyl | galloyl | galloyl | galloyl | in which galloyl denotes

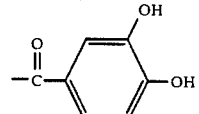

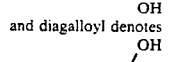

and digalloyl denotes

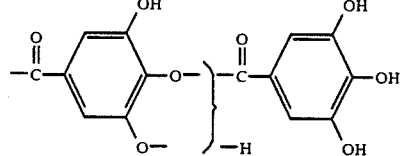

methyl gallate and gallic acid and the pharmaceutically acceptable salts, ethers and esters hereof, together with pharmaceutically acceptable carrier and dilution agents, in an amount of active substances of between about 0.1 μg to 500 mg per kilogram of body weight.

2. The method for treating inflammatory diseases, according to claim 1, wherein antiphlogistic pharmaceutical preparation additionally comprises gallic acid, gallic acid methyl ester, or a salt, ether or ester thereof.

3. The method for treating inflammatory diseases according to claim 2, wherein the antiphlogistic pharmaceutical preparation comprises tetragalloylquinic acid or a salt, ether or ester thereof.

4. The method for treating inflammatory diseases, according to claim 1, wherein the antiphlogistic pharmaceutical preparation comprises at least one of said compounds, obtained by the method comprising the steps of:
   (a) extracting a comminuted Galphimia glauca material with alkanols having from 1 to 3 carbon atoms, followed by at removing at least part of the extraction medium from the extract;
   (b) diluting of the extract with water and extracting the diluted mixture with chlorinated hydrocarbons having a boiling point not exceeding 120° C.;
   (c) extracting the aqueous phase obtained from step (b) with a $C_1$-$C_4$ alkyl ester of acetic acid and isolating the components contained in the acetic acid ester phase; and
   (d) subjecting the hydrophilic components obtained in step (c) to column chromatography to isolate the lipophilic components thereof.

5. The method for treating inflammatory diseases, according to claim 4, wherein the antiphlogistic pharmaceutical preparation is obtained by a method further comprising the step of:
   subjecting the acetic acid ester extract obtained from step (c) to acid hydrolysis,
   wherein step (d) comprises subjecting the acid hydrolysed hydrophilic components to chromatography via a silica gel column using a solvent system consisting essentially of ethyl acetate/methanol/water/formic acid and then isolating the lipophilic components be means of HPLC-RP chromatography using a solvent system consisting essentially of acetonitrile/water.

6. The method for treating inflammatory diseases, by administering the pharmaceutical preparation according to claim 1 comprising active substances in an amount of between about 0.5 mg to 500 mg per kilogram of body weight.

7. The method for treating inflammatory diseases by administering the pharmaceutical preparation according to claim 1 comprising active substances in an amount of between about 0.5 mg to 50 mg per kilogram of body weight.

8. The method for treating inflammatory diseases by administering the pharmaceutical preparation according to claim 1 comprising active substances in an amount of between about 5 mg to 25 mg per kilogram of body weight.

9. The method for treating inflammatory diseases, by administering the pharmaceutical preparation according to claim 1 comprising a unit dosage form having active substances in an amount of between 100 mg to 1.

10. A method of treating inflammatory diseases comprising administering a prophylactic dose of a composition according to claim 1.

11. The method according to claim 10, wherein said inflammatory disease consists of a condition selected from the group consisting of rheumatic disease, allergic disease, bronchial asthma, obstructive bronchitis, inflammatory pulmonary disease, inflammatory vascular processes and inflammatory skin disease.

12. The method according to claim 10, wherein said inflammatory disease comprises asthma.

13. The method for treating inflammatory diseases, by administering the pharmaceutical preparation according to claim 1 comprising as active substances gallic acid, gallic acid methyl ester and tetragalloylquinic acid or pharmaceutically acceptable salts thereof in a quantitative ratio of about 2.5:2.5:10.

* * * * *